United States Patent [19]

Niebur

[11] Patent Number: 5,567,861
[45] Date of Patent: Oct. 22, 1996

[54] INBRED CORN LINE PHN46

[75] Inventor: William S. Niebur, Victor, France

[73] Assignee: Pioneer Hi-Bred International, Inc., Des Moines, Iowa

[21] Appl. No.: 101,808

[22] Filed: Aug. 3, 1993

Related U.S. Application Data

[63] Continuation of Ser. No. 542,353, Jun. 20, 1990, abandoned.
[51] Int. Cl.$^6$ .............................. A01H 5/00; A01H 4/00; C12N 5/04
[52] U.S. Cl. ................. 800/200; 800/250; 800/DIG. 56; 47/58; 47/DIG. 1; 435/240.4; 435/240.45; 435/240.5
[58] Field of Search .................................. 800/200, 250, 800/DIG. 56; 435/240.4, 240.45, 240.49, 240.5; 47/58.03, 58.05

[56] References Cited

PUBLICATIONS

Hallauer et al. *Corn Breeding* In Corn & Corn Improvement ASA publication #18, 3rd edition—Editor G. L. Sprague pp. 463–481, 482–487, 554–564.

Phillips et al. (1988) "Cell/tissue Culture and In Vitro Manipulation" In/ Corn & Corn Improvement. ASA Publications #18 3rd Ed. pp. 347–349 & 356–357.

Troyer et al. (1985) "Selection for Early Flowering in Corn: 10 Late Synthetics" Crop Science vol. 25 pp. 695–697.

Paelhnon (1987) *Breeding Field Crops*. AUI Publishing Co. Westport Ct. pp. 237–246.

Meghji et al. "Inbreeding Depression, Inbred & Hybrid Grain Yields..." Crop Science vol. 24, (1984) pp. 545–549.

Phillips et al. (1987) In Corn & Corn Improvement, ASA publication #187 3rd Edition. Sprague et al. editor p. 358.

*Primary Examiner*—Gary Benzion
*Attorney, Agent, or Firm*—Pioneer Hi-Bred International, Inc.

[57] ABSTRACT

According to the invention, there is provided an inbred corn line, designated PHN46. This invention thus relates to the plants and seeds of inbred corn line PHN46 and to methods for producing a corn plant produced by crossing the inbred line PHN46 with itself or with another corn plant. This invention further relates to hybrid corn seeds and plants produced by crossing the inbred line PHN46 with another corn line or plant and to crosses with related species.

8 Claims, No Drawings

INBRED CORN LINE PHN46

This is a continuation of application Ser. No. 07/542,353 filed on Jun. 20, 1990, now abandoned.

FIELD OF THE INVENTION

This invention is in the field of corn breeding, specifically relating to an inbred corn line designated PHN46.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population.

Typically, however, the genotype of neither the parents nor the desired genotype is known in any detail.

SUMMARY OF THE INVENTION

According to the invention, there is provided a novel inbred corn line, designated PHN46. This invention thus relates to the seeds of inbred corn line PHN46, to the plants of inbred corn line PHN46, and to methods for producing a corn plant produced by crossing the inbred line PHN46 with itself or another corn line. This invention further relates to hybrid corn seeds and plants produced by crossing the inbred line PHN46 with another corn line or a related species.

DEFINITIONS

In the description and examples that follow, a number of terms are used herein. In order to provide a clear and consistent understanding of the specification and claims, including the scope to be given such terms, the following definitions are provided:

ABS=absolute measurement and % MN is percentage of mean of the experiments in which inbred or hybrid was grown unless otherwise defined.

BAR PLT=BARREN PLANTS. This is the percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the inbred or hybrid was grown.

CLD TST=COLD TEST. This is the percentage of kernels that germinate under cold soil conditions.

COB SC=COB SCORE. The cob score is a rating of how well the grain is shelled off the cob and how badly the cob is broken up going through the combine. This is given as a 1 to 9 score with 9 being very good. A high score indicates that the grain shells off of the cob well, and the cob does not break.

DRP EAR=DROPPED EARS. This is a measure of the number of dropped ears per plot and represents the percentage of plants that did not drop ears prior to harvest.

EAR HT=EAR HEIGHT. The ear height is a measure from the ground to the top developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN QUL=GRAIN QUALITY. This is a 1 to 9 rating for the general quality of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

PRM=PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV= Maize Dwarf Mosaic Virus & MCDV=Maize Chlorotic Dwarf Virus): Visual rating (1–9 score) where a "1" is very susceptible and a "9" is very resistant.

COM SMT=Common Smut (*Ustilago maydis*): Percentage of plants that did not have infection.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

EYE SPT=Eyespot (*Kabatiella zeae*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Inbred corn line PHN46 is a yellow, dent corn inbred that provides an acceptable male parental line in crosses for producing first generation F1 corn hybrids. PHN46 is best adapted to the Central Corn Belt of the United States. The inbred can be used to produce hybrids from approximately 110–122 relative maturity based on the Minnesota Relative Maturity Rating System for harvest moisture of grain. PHN46 should make an excellent male since it has high pollen yield. The inbred in hybrid combination has good yield, stay green, stalks, and roots.

The inbred has shown uniformity and stability within the limits of environmental influence for all the traits as described in the Variety Description Information (Table 1) that follows. Most of the data in the Variety Description Information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHN46.

Inbred corn line PHN46, being substantially homozygous, can be reproduced by planting seeds of the line, growing the resulting corn plants under self-pollinating or sib-pollinating conditions with adequate isolations, and harvesting the resulting seed, using techniques familiar to the agricultural arts.

TABLE

VARIETY DESCRIPTION INFORMATION
INBRED = PHN46

| Type: Dent | Region Best Adapted: Central Corn Belt |
|---|---|

A. Maturity: Average across maturity zones. Zone: 0

Heat Unit Shed: 1510
Heat Unit Silk: 1520
No. Reps: 40

$$\text{HEAT UNITS} = \frac{[\text{Max. Temp. } (<\_86° \text{ F.}) + \text{Min. Temp } (>\_50° \text{ F.})]*}{2} - 50$$

*If maximum is greater than 86 degrees fahrenheit, then 86 is used and if minimum is less than 50, then 50 is used. Heat units accumulated daily and can not be less than 0.

B. Plant Characteristics:

Plant height (to tassel tip): 198 cm
Length of top ear internode: 12 cm
Number of ears per stalk: Slight Two-ear Tendency
Ear height (to base of top ear): 77 cm
Number of tillers: None
Cytoplasm type: Normal C. Leaf:

Color: (WF9) Medium Green
Angle from Stalk: 30-60 degrees
Marginal Waves: (WF9) Few
Number of Leaves (mature plants): 18
Sheath Pubescence: (W22) Light
Longitudinal Creases: (OH56A) Few
Length (Ear node leaf): 65 cm
Width (widest point, ear node leaf): 10 cm

TABLE-continued

VARIETY DESCRIPTION INFORMATION
INBRED = PHN46

| Type: Dent | Region Best Adapted: Central Corn Belt |
|---|---|

D. Tassel:

Number lateral branches: 4
Branch Angle from central spike: >45 degrees
Pollen Shed: Heavy based on Pollen Yield Test
(107% of experiement means)
Peduncle Length (top leaf to basal branches): 20 cm
Anther Color: Pink
Glume Color: Green E. Ear (Husked Ear Data Except When Stated Otherwise):

Length: 15 cm
Weight: 103 gm
Mid-point Diameter: 44 mm
Silk Color: Yellow
Husk Extension (Harvest stage): Long (8–10 cm)
Husk Leaf: Short (<8 cm)
Taper of Ear: Slight
Position of Shank (dry husks): Upright
Kernel Rows: Straight, Distinct Number = 14
Husk Color (fresh): Light Green
Husk Color (dry): Buff
Shank Length: 13 cm
Shank (No. of internodes): 8

F. Kernel (Dried):

Size (from ear mid-point)
Length: 10 mm
Width: 8 mm
Thick: 4 mm
Shape Grade (% rounds): <20 (16% medium round based on Parent Test Data)
Pericarp Color: Colorless
Aleurone Color: Homozygous Yellow
Endosperm Color: Yellow
Endosperm Type: Normal Starch
Gm Wt/100 Seeds (unsized): 33 gm G. Cob:

Diameter at mid-point: 24 mm
Strength: Strong
Color: Red

H. Diseases:

Corn Lethal Necrosis (MCMV = Maize Chlorotic Mottle Virus and MDMV = Maize Dwarf Mosaic Virus): Intermediate
Maize Dwarf Mosaic Complex (MDMV & MCDV = Maize Dwarf Virus): Intermediate
Anthracnose Stalk Rot (*C. graminicola*): Intermediate
S. Leaf Blight (*H. maydis*): Intermediate
N. Leaf Blight (*H. turcicum*): Intermediate
Eye Spot (*K. zeae*): Intermediate
Gray Leaf Spot (*C. zeae*): Susceptible
Stewart's Wilt (*E. stewartii*): Resistant
Goss's Wilt (*C. nebraskense*): Highly Resistant
Common Smut (*U. maydis*): Highly Resistant
Head Smut (*S. reiliana*): Resistant
Fusarium Ear Mold (*F. moniliforme*): Resistant I. Insects:

European Corn Borer-1 Leaf Damage (Pre-flowering): Susceptible
European Corn Borer-2 (Post-flowering): Intermediate
The above descriptions are based on a scale of 1–9, 1 being highly susceptible, 9 being highly resistant.
S (Susceptible): Would generally represent a score of 1–3.
I (Intermediate): Would generally represent a score of 4–5.
R (Resistant): Would generally represent a score of 6–7.
H (Highly Resistant): would generally represent a score of 8–9. Highly resistant does not imply the inbred is immune J. Variety Most Closely Resembling:

| Character | Inbred |
|---|---|
| Maturity | PHZ51 |
| Usage | PHV78 |

Data for Items B, C, D, E, F, and G is based primarily on a maximum of two reps from Johnston, Iowa grown in 1989, plus description information from the maintaining station.

ELECTROPHORESIS RESULTS

Isozyme Genotypes for PHN46

Isozyme data were generated for inbred corn line PHN46 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays* L.)", Technical Bulletin No. 286, North Carolina Agricultural Research Service, North Carolina State University, Raleigh, N.C. (1988).

The data in Table 2 compares PHN46 with its parents, PHZ51 and PHV78.

TABLE 2

ELECTROPHORESIS RESULTS FOR PHN46 AND ITS PARENTS PHZ51 AND PHV78

| | | PARENTS | |
|---|---|---|---|
| Loci | PHN46 | PHZ51 | PHV78 |
| ACP1 | 3 | 3 | 2 |
| ADH1 | 4 | 4 | 4 |
| CAT3 | 9 | 9 | 9 |
| DIA1 | 8 | 8 | 8 |
| GOT1 | 4 | 4 | 4 |
| GOT2 | 4 | 4 | 4 |
| GOT3 | 4 | 4 | 4 |
| IDH1 | 4 | 4 | 4 |
| IDH2 | 6 | 6 | 6 |
| MDH1 | 6 | 6 | 1 |
| MDH2 | 3.5 | 3.5 | 3.5 |
| MDH3 | 18 | 18 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 4 | 4 | 3 |
| PGD1 | 2 | 2 | 3.8 |
| PGD2 | 5 | 5 | 5 |
| PHI1 | 4 | 4 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHN46. Further, both first and second parent corn plants can come from the inbred corn line PHN46. Thus, any such methods using the inbred corn line PHN46 are part of this invention: selfing, backcrosses, hybrid production, crosses to populations, and the like. All plants produced using inbred corn line PHN46 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, at 367–372). Thus, another aspect of this invention is to provide cells which upon growth and differentiation produce the inbred line PHN46.

The utility of inbred line PHN46 also extends to crosses with other species. Commonly, suitable species will be of the family Graminaceae, and especially of the genera Zea, Tripsacum, Coix, Schlerachne, Polytoca, Chionachne, and Trilobachne, of the tribe Maydeae. Of these, Zea and Tripsacum, are most preferred. Potentially suitable for crosses with PHN46 may be the various varieties of grain sorghum, *Sorghum bicolor* (L.) Moench.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHN46, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE

Inbred and Hybrid Performance of PHN46

In the examples that follow the traits and characteristics of inbred corn line PHN46 are given as a line and in hybrid combination. The data collected on inbred corn line PHN46 is presented for the key characteristics and traits.

The results in Table 3A compare PHN46 to its PHZ51 parent. PHN46 yields significantly more, is shorter, and sheds (GDU SHD) pollen later but silks (GDU SLK) earlier than PHZ51. PHN46 and PHZ51 have similar pollen yield and tassel size. PHN46 has better common smut resistance but is more susceptible to root lodging and first and second brood European corn borer than PHZ51.

Table 3B compares PHN46 to its other parent, PHV78. PHN46 yields more, has higher test weight, and less grain moisture at maturity than PHV78. PHN46 is a shorter inbred with lower ear placement and flowers (GDU SHD and GDU SLK) earlier than PHV78. PHN46 has significantly better seedling vigor and early stand establishment than PHV78. PHN46 has less pollen yield and its tassel is smaller than PHV78. The PHN46 inbred is more resistant to common smut, ear mold, and Stewart's wilt but less resistant to first and second brood European corn borer than PHV78.

The results in Table 3C show that PHN46 has higher yield, slightly lower test weight, and higher grain harvest moisture than PHR62. PHN46 is shorter with lower ear placement and flowers (GDU SHD and GDU SLK) earlier than PHR62. PHN46 has better seedling vigor and early stand count, similar pollen yield, and a smaller tassel than PHR62. Common rust and Stewart's wilt resistance is better for PHN46 but it is more susceptible to stalk and root lodging, ear mold, and first and second brood European corn borer than PHR62.

Table 3D shows that PHN46 is lower yielding, has higher test weight, and lower grain moisture at maturity than PHN82. PHN46 is taller with higher ear placement, sheds pollen (GDU SHD) later, and silks (GDU SLK) similarly compared to PHN82. PHN46 has better seedling vigor, similar early stand establishment, greater pollen yield, and a bigger tassel than PHN82. Southern corn leaf blight and Stewart's wilt are slightly more resistant in PHN46 but it is more susceptible to stalk and root lodging, common smut, and first and second brood European corn borer than PHN82.

The results in Table 4A compare PHN46 to PHZ51 crossed to the same inbred testers. The hybrids are similar for yield and test weight but PHN46 has higher grain harvest moisture. PHN46 hybrids are shorter but have slightly higher ear height and flower (GDU SHD) later than PHZ51 hybrids. The PHN46 hybrids have less stay green, similar stalks, and are less prone to root lodge than PHZ51 hybrids.

Table 4B compares PHN46 to PHR62 crossed to the same inbred testers. The PHN46 hybrids have higher yield, similar test weight, and more grain harvest moisture compared to PHR62 hybrids. The hybrids have similar plant and ear height and flowering (GDU SHD) is similar. PHN46 hybrids have better stay green, stalks, and roots than PHR62 hybrids.

The results in Table 4C compare PHN46 to PHN82 crossed to the same inbred testers. The PHN46 hybrids have lower yield, test weight, and grain moisture at maturity than PHN82 hybrids. The hybrids have similar height but the PHN46 hybrids have higher ear placement. The PHN46 hybrids have significantly better cob scores and slightly better stalks than the PHN82 hybrids.

The results in Table 4D compare PHN46 to PHV78 crossed to the same inbred testers. The PHN46 hybrids have higher yield, similar test weight, and less grain moisture at harvest than the PHV78 hybrids. The PHN46 hybrids are slightly shorter but have higher ear placement and flower (GDU SHD) earlier than the PHV78 hybrids. PHN46 hybrids have better stay green and root lodging resistance and have similar stalks compared to the PHV78 hybrids.

Tables 5–10 compare PHN46 hybrids to Pioneer Brand Hybrids 3374, 3504, 3527, 3362, 3180, and 3344, respectively. Each hybrid has a parent in common with the PHN46 hybrid other than PHN46. The hybrids are adapted to much of the same area as the PHN46 hybrids. Table 5 compares a PHN46 hybrid with 3374. The PHN46 hybrid has higher yield, lower test weight, and more grain moisture at maturity than 3374. The PHN46 hybrid is shorter and flowers (GDU SHD) later than 3374. The PHN46 hybrid has better roots but poorer stalks than 3374.

Table 6 results show the PHN46 hybrid has similar yield and test weight but higher grain moisture at maturity than 3504. The PHN46 hybrid is shorter with higher ear placement and flowers (GDU SHD) later than 3504. The PHN46 hybrid has slightly better stay green, better root lodging resistance, and slightly less stalk lodging resistance than 3504.

The results in Table 7 show the PHN46 hybrid yields more, has lower test weight, and contains more grain moisture at maturity than 3527. The PHN46 hybrid is shorter and flowers (GDU SHD) later than 3527. Stay green is better for the PHN46 hybrid and it has similar stalks but better roots compared to 3527.

Table 8 compares a PHN46 hybrid to 3362. The PHN46 hybrid has higher yield and lower test weight and grain harvest moisture than 3362. The PHN46 hybrid is taller with higher ear placement and flowers (GDU SHD) later than 3362. The PHN46 hybrid has slightly lower seedling vigor but has better early stand establishment than 3362. The PHN46 hybrid has slightly better stay green and has better stalk and root lodging resistance than 3362.

The results in Table 9 show a PHN46 hybrid has significantly higher yield, better test weight, and lower grain moisture at maturity than 3180. The PHN46 hybrid is shorter with lower ear placement and flowers (GDU SHD) earlier than 3180. The PHN46 hybrid has slightly lower vigor but has significantly higher early stand count and has better stalk and root lodging resistance than 3180.

Table 10 results compare a PHN46 hybrid to 3344. The PHN46 hybrid yields significantly more, has higher test weight, and contains less grain moisture at maturity than 3344. The PHN46 hybrid is shorter but ear height is similar and it flowers (GDU SHD) earlier than 3344. The seedling vigor is less but early stand count is greater for the PHN46 hybrid than 3344. The PHN46 hybrid has better stalk and root lodging resistance than 3344.

The results above show that PHN46 is a good inbred and does well in hybrid combination. This inbred will have an impact in the region it is adapted.

TABLE 3A

PAIRED INBRED COMPARISON DATA
VARIETY #1 - PHN46
VARIETY #2 - PHZ51

| YEAR | REGION | VAR # | YLD SC ABS | EAR SZ ABS | BAR PLT ABS | PLT HT ABS | EAR HT ABS | SDG VGR ABS | EST CNT ABS | TIL LER ABS | GDU SHD ABS | GDU SLK ABS | POL SC ABS |
|---|---|---|---|---|---|---|---|---|---|---|---|---|---|
| TOTAL SUM | | 1 | 5.7 | 5.6 | 97.1 | 72.6 | 27.8 | 6.1 | 26.9 | 2.3 | 146.7 | 149.3 | 5.8 |
| | | 2 | 4.3 | 5.0 | 86.4 | 83.6 | 29.6 | 5.4 | 28.6 | 0.4 | 145.2 | 150.5 | 6.0 |
| | | LOCS | 15 | 9 | 3 | 8 | 8 | 21 | 25 | 11 | 31 | 32 | 11 |
| | | DIFF | 1.4 | 0.6 | 10.7 | 11.0 | 1.9 | 0.7 | 1.7 | 1.9 | 1.4 | 1.2 | 0.2 |
| | | PROB | .002# | .179 | .506 | .000# | .613 | .012+ | .051* | .242 | .123 | .174 | .714 |

| YEAR | REGION | VAR # | TAS SZ ABS | TEX EAR ABS | SCT GRN ABS | STA GRN ABS | RT LDG ABS | COM RST ABS | EAR MLD ABS | STW WLT ABS | ECB 1LF ABS | ECB 2SC ABS |
|---|---|---|---|---|---|---|---|---|---|---|---|---|
| TOTAL SUM | | 1 | 4.9 | 5.7 | 6.4 | 4.1 | 40 | 8.0 | 7.6 | 7.0 | 5.2 | 4.4 |
| | | 2 | 5.5 | 5.9 | 6.3 | 4.4 | 90.1 | 6.0 | 7.1 | 7.0 | 6.8 | 6.2 |
| | | LOCS | 15 | 7 | 14 | 7 | 1 | 1 | 13 | 1 | 19 | 5 |
| | | DIFF | 0.5 | 0.1 | 0.1 | 0.3 | 50.0 | 2.0 | 0.5 | 0.0 | 1.6 | 1.8 |
| | | PROB | .164 | .805 | .729 | .689 | | | .151 | | .000# | .105 |

*= 10% SIG
+= 5% SIG
= 1% SIG

TABLE 3B

PAIRED INBRED COMPARISON DATA
VARIETY #1 - PHN46
VARIETY #2 - PHV78

| YEAR | REGION | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | TIL LER ABS | GDU SHD ABS | GDU SLK ABS |
|---|---|---|---|---|---|---|---|---|---|---|---|---|---|---|---|
| TOTAL SUM | | 1 | 64.8 | 140 | 5.9 | 29.5 | 5.4 | 95.6 | 72.1 | 27.6 | 6.2 | 29.2 | 2.0 | 146.8 | 148.8 |
| | | 2 | 40.5 | 88 | 6.9 | 31.9 | 6.9 | 91.6 | 84.6 | 30.5 | 4.9 | 25.3 | 2.4 | 153.8 | 158.4 |

TABLE 3B-continued

PAIRED INBRED COMPARISON DATA
VARIETY #1 - PHN46
VARIETY #2 - PHV78

|  |  |  | LOCS | 1 | 1 | 15 | 1 | 10 | 5 | 10 | 10 | 21 | 23 | 13 | 35 | 32 |
|---|---|---|---|---|---|---|---|---|---|---|---|---|---|---|---|---|
|  |  |  | DIFF | 24.3 | 53 | 0.9 | 2.4 | 1.5 | 4.0 | 12.5 | 2.9 | 1.4 | 3.9 | 0.4 | 7.1 | 9.7 |
|  |  |  | PROB |  |  | .063* |  | .001# | .471 | .001# | .295 | .004# | .000# | .693 | .000# | .000# |

| YEAR | REGION | VAR # | POL SC ABS | TAS SZ ABS | TEX EAR ABS | TST WT ABS | SCT GRN ABS | STA GRN ABS | BRT STK ABS | COM RST ABS | EAR MLD ABS | SLF BLT ABS | STW WLT ABS | ECB 1LF ABS | ECB 2SC ABS |
|---|---|---|---|---|---|---|---|---|---|---|---|---|---|---|---|
| TOTAL SUM |  | 1 | 5.8 | 5.0 | 5.3 | 49.1 | 6.5 | 2.4 | 100.0 | 8.0 | 7.5 | 5.0 | 7.0 | 4.9 | 4.4 |
|  |  | 2 | 7.4 | 7.4 | 4.3 | 47.1 | 5.9 | 5.0 | 100.0 | 6.0 | 6.5 | 5.0 | 6.0 | 6.1 | 4.4 |
|  |  | LOCS | 13 | 15 | 6 | 1 | 13 | 8 | 1 | 1 | 11 | 1 | 1 | 17 | 5 |
|  |  | DIFF | 1.6 | 2.4 | 1.0 | 2.0 | 0.6 | 2.6 | 0.0 | 2.0 | 1.1 | 0.0 | 1.0 | 1.2 | 0.0 |
|  |  | PROB | .032+ | .000# | .296 |  | .104 | .005# |  |  | .031+ |  |  | .001# | .000# |

\*= 10% SIG
+= 5% SIG
= 1% SIG

TABLE 3C

PAIRED INBRED COMPARISON DATA
VARIETY #1 - PHN46
VARIETY #2 - PHR62

| YEAR | REGION | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS |
|---|---|---|---|---|---|---|---|---|---|---|---|---|---|---|
| TOTAL SUM |  |  | 54.6 | 124 | 5.8 | 20.8 | 5.6 | 84.0 | 70.0 | 27.7 | 6.0 | 32.2 | 100.0 | 2.0 |
|  |  | 2 | 42.9 | 92 | 5.4 | 19.4 | 5.8 | 85.5 | 80.8 | 32.9 | 4.4 | 29.1 | 99.2 | 2.4 |
|  |  | LOCS | 4 | 4 | 16 | 4 | 9 | 6 | 12 | 12 | 22 | 31 | 3 | 13 |
|  |  | DIFF | 11.8 | 32 | 0.4 | 1.5 | 0.2 | 1.5 | 10.8 | 5.2 | 1.6 | 3.1 | 0.8 | 0.4 |
|  |  | PROB | .008# | .104 | .456 | .355 | .559 | .887 | .003# | .030+ | .000# | .001# | .423 | .714 |

| YEAR | REGION | VAR # | GDU SHD ABS | GDU SLK ABS | POL SC ABS | TAS SZ ABS | TEX EAR ABS | TST WT ABS | GRN QUL ABS | SCT GRN ABS | STA GRN ABS | STK LDG ABS | RT LDG ABS | BRT STK ABS |
|---|---|---|---|---|---|---|---|---|---|---|---|---|---|---|
| TOTAL SUM |  | 1 | 147.4 | 149.9 | 5.8 | 4.9 | 5.7 | 54.3 | 6.2 | 6.4 | 3.8 | 90.8 | 60.8 | 100.0 |
|  |  | 2 | 148.6 | 154.0 | 5.8 | 6.2 | 7.7 | 55.1 | 6.0 | 6.4 | 5.8 | 99.3 | 78.6 | 100.0 |
|  |  | LOCS | 39 | 36 | 12 | 15 | 7 | 4 | 3 | 14 | 10 | 3 | 4 | 1 |
|  |  | DIFF | 1.2 | 4.1 | 0.0 | 1.3 | 2.0 | 0.8 | 0.2 | 0.1 | 2.1 | 8.5 | 17.9 | 0.0 |
|  |  | PROB | .261 | .000# | .000# | .000# | .010+ | .373 | .899 | .895 | .021+ | .333 | .518 |  |

| YEAR | REGION | VAR # | COM RST ABS | EAR MLD ABS | STW WLT ABS | ECB DPE ABS | ECB 1LF ABS | ECB 2SC ABS |
|---|---|---|---|---|---|---|---|---|
| TOTAL SUM |  | 1 | 8.0 | 7.6 | 7.0 | 100.0 | 5.1 | 5.4 |
|  |  | 2 | 5.0 | 8.2 | 6.0 | 98.8 | 7.0 | 6.5 |
|  |  | LOCS | 1 | 13 | 1 | 2 | 20 | 7 |
|  |  | DIFF | 3.0 | 0.5 | 1.0 | 1.3 | 2.0 | 1.1 |
|  |  | PROB | .089* |  | .500 | .000# | .103 |  |

\*= 10% SIG
+= 5% SIG
= 1% SIG

TABLE 3D

PAIRED INBRED COMPARISON DATA
VARIETY #1 - PHN46
VARIETY #2 - PHN82

| VAR | BU ACR | BU ACR | YLD SC | MST | EAR SZ | BAR PLT | PLT HT | EAR HT | SDG VGR | EST CNT | DRP EAR | TIL LER |
|---|---|---|---|---|---|---|---|---|---|---|---|---|

TABLE 3D-continued

PAIRED INBRED COMPARISON DATA
VARIETY #1 - PHN46
VARIETY #2 - PHN82

| YEAR | REGION | # | ABS | % MN | ABS | ABS | ABS | ABS | ABS | ABS | ABS | ABS | ABS | ABS |
|---|---|---|---|---|---|---|---|---|---|---|---|---|---|---|
| TOTAL | | 1 | 51.8 | 122 | 5.9 | 19.1 | 5.4 | 88.2 | 70.5 | 27.9 | 6.1 | 34.2 | 100.0 | 1.6 |
| SUM | | 2 | 70.7 | 173 | 6.9 | 24.3 | 6.2 | 97.7 | 65.0 | 25.0 | 4.5 | 34.4 | 100.0 | 0.9 |
| | | LOCS | 9 | 9 | 15 | 9 | 10 | 8 | 15 | 15 | 30 | 35 | 6 | 16 |
| | | DIFF | 18.8 | 51 | 0.9 | 5.2 | 0.8 | 9.5 | 5.5 | 2.9 | 1.6 | 0.2 | 0.0 | 0.7 |
| | | PROB | .001# | .002# | .014+ | .001# | .053* | .031+ | .001# | .039+ | .000# | .806 | 1.00 | .598 |

| YEAR | REGION | VAR # | GDU SHD ABS | GDU SLK ABS | POL SC ABS | TAS SZ ABS | TEX EAR ABS | TST WT ABS | GRN QUL ABS | SCT GRN ABS | STA GRN ABS | STK LDG ABS | RT LDG ABS | BRT STK ABS |
|---|---|---|---|---|---|---|---|---|---|---|---|---|---|---|
| TOTAL | | 1 | 147.7 | 149.3 | 5.8 | 5.1 | 5.6 | 55.8 | 6.6 | 6.5 | 2.8 | 95.3 | 73.1 | 100.0 |
| SUM | | 2 | 143.9 | 149.4 | 4.7 | 4.5 | 5.4 | 54.6 | 6.1 | 7.1 | 6.5 | 99.5 | 95.5 | 100.0 |
| | | LOCS | 42 | 39 | 13 | 17 | 7 | 9 | 5 | 14 | 13 | 6 | 6 | 1 |
| | | DIFF | 3.8 | 0.1 | 1.1 | 0.6 | 0.1 | 1.2 | 0.5 | 0.6 | 3.7 | 4.2 | 22.4 | 0.0 |
| | | PROB | .000# | .962 | .028+ | .181 | .838 | .070* | .611 | .071* | .000# | .319 | .154 | |

| | | YEAR | REGION | VAR # | COM RST ABS | EAR MLD ABS | SLF BLT ABS | STW WLT ABS | ECB DPE ABS | ECB 1LF ABS | ECB 2SC ABS |
|---|---|---|---|---|---|---|---|---|---|---|---|
| | | TOTAL | | 1 | 8.0 | 7.7 | 5.0 | 7.0 | 100.0 | 4.9 | 4.6 |
| | | SUM | | 2 | 9.0 | 7.2 | 4.0 | 6.0 | 100.0 | 5.1 | 5.9 |
| | | | | LOCS | 1 | 12 | 1 | 1 | 2 | 18 | 7 |
| | | | | DIFF | 1.0 | 0.5 | 1.0 | 1.0 | 0.0 | 0.1 | 1.3 |
| | | | | PROB | | .293 | | | 1.00 | .808 | .382 |

*= 10% SIG
+= 5% SIG
= 1% SIG

TABLE 4A

AVERAGE INBRED BY TESTER PERFORMANCE COMPARING PHN46 TO PHZ51 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/AC).

| | INBRED | PRM | SEL IND | BU ACR | YLD | MST | GDU SRD | PRM SHD | STK LDG | RT LDG | BAR PLT |
|---|---|---|---|---|---|---|---|---|---|---|---|
| TOTAL | REPLIC. | 53 | 57 | 57 | 57 | 57 | 18 | 65 | 49 | 28 | 4 |
| MEAN WTS | PHN46 | 115 | 104 | 151 | 101 | 101 | 101 | 122 | 103 | 108 | 100 |
| MEAN WTS | PHZ51 | 112 | 106 | 152 | 101 | 97 | 99 | 116 | 104 | 101 | 101 |
| | DIFF. | 3 | 2 | 1 | 0 | 4 | 2 | 6 | 1 | 7 | 1 |

| | INBRED | STA GRN | TST WTA | GRN QUL | SDG VGR | EST CNT | STK CNT | PLT HT | EAR HT | DRP EAR | BRT STK |
|---|---|---|---|---|---|---|---|---|---|---|---|
| TOTAL | REPLIC. | 32 | 57 | 45 | 37 | 40 | 62 | 30 | 30 | 39 | 8 |
| MEAN WTS | PHN46 | 105 | 99 | 97 | 92 | 94 | 98 | 98 | 107 | 101 | 102 |
| MEAN WTS | PHZ51 | 109 | 100 | 102 | 96 | 100 | 99 | 103 | 105 | 99 | 103 |
| | DIFF. | 4 | 1 | 5 | 5 | 5 | 2 | 5 | 2 | 1 | 1 |

TABLE 4B

AVERAGE INBRED BY TESTER PERFORMANCE COMPARING PHN46 TO PHR62 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/AC).

| INBRED | PRM | SEL IND | BU ACR | YLD | MST | GDU SHD | PRM SHD | STK LDG | RT LDG | BAR PLT | STA GRN |
|---|---|---|---|---|---|---|---|---|---|---|---|

TABLE 4B-continued

AVERAGE INBRED BY TESTER PERFORMANCE COMPARING PHN46 TO PHR62 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/AC).

| | | | | | | | | | | | |
|---|---|---|---|---|---|---|---|---|---|---|---|
| TOTAL | REPLIC. | 130 | 130 | 136 | 136 | 136 | 39 | 142 | 115 | 69 | 12 | 69 |
| MEAN WTS | PHN46 | 116 | 107 | 162 | 104 | 100 | 102 | 123 | 104 | 106 | 100 | 117 |
| MEAN WTS | PHR62 | 111 | 100 | 155 | 99 | 93 | 100 | 120 | 100 | 94 | 100 | 93 |
| | DIFF. | 5 | 7 | 8 | 6 | 7 | 2 | 3 | 4 | 12 | 0 | 24 |

| | INBRED | TST WTA | COB SC | GRN QUL | SDG VGR | EST CNT | STK CNT | PLT HT | EAR HT | DRP EAR | BRT STK |
|---|---|---|---|---|---|---|---|---|---|---|---|
| TOTAL | REPLIC. | 136 | 4 | 107 | 60 | 83 | 138 | 65 | 65 | 75 | 22 |
| MEAN WTS | PHN46 | 99 | 90 | 95 | 100 | 98 | 100 | 99 | 102 | 100 | 98 |
| MEAN WTS | PHR62 | 100 | 120 | 106 | 106 | 100 | 100 | 101 | 103 | 100 | 96 |
| | DIFF. | 1 | 31 | 11 | 5 | 1 | 0 | 2 | 2 | 0 | 2 |

TABLE 4C

AVERAGE INBRED BY TESTER PERFORMANCE COMPARING PHN46 TO PHN82 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/AC).

| | INBRED | PRM | SEL IND | BU ACR | YLD | MST | GDU SHD | PRM SHD | STK LDG | RT LDG | BAR PLT | STA GRN |
|---|---|---|---|---|---|---|---|---|---|---|---|---|
| TOTAL | REPLIC. | 72 | 72 | 72 | 72 | 72 | 21 | 76 | 62 | 38 | 8 | 38 |
| MEAN WTS | PHN46 | 115 | 105 | 158 | 102 | 96 | 100 | 121 | 102 | 109 | 99 | 103 |
| MEAN WTS | PHN82 | 119 | 109 | 164 | 105 | 103 | 99 | 120 | 99 | 110 | 99 | 116 |
| | DIFF. | 4 | 4 | 6 | 3 | 7 | 1 | 2 | 3 | 1 | 0 | 13 |

| | INBRED | TST WTA | COB SC | GRN QUL | SDG VGR | EST CNT | STK CNT | PLT HT | EAR HT | DRP EAR | BRT STK |
|---|---|---|---|---|---|---|---|---|---|---|---|
| TOTAL | REPLIC. | 72 | 2 | 36 | 30 | 38 | 74 | 38 | 38 | 50 | 22 |
| MEAN WTS | PHN46 | 98 | 97 | 99 | 95 | 100 | 100 | 98 | 103 | 100 | 100 |
| MEAN WTS | PHN82 | 100 | 58 | 104 | 95 | 101 | 101 | 97 | 93 | 100 | 99 |
| | DIFF. | 2 | 39 | 5 | 1 | 1 | 1 | 1 | 9 | 0 | 1 |

TABLE 4D

AVERAGE INBRED BY TESTER PERFORMANCE COMPARING PHN46 TO PHV78 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/AC).

| | INBRED | PRM | SEL IND | BU ACR | YLD | MST | GDU SHD | PRM SHD | STK LDG | RT LDG | BAR PLT |
|---|---|---|---|---|---|---|---|---|---|---|---|
| TOTAL | REPLIC. | 19 | 19 | 19 | 19 | 19 | 5 | 17 | 18 | 5 | 2 |
| MEAN WTS | PHN46 | 119 | 109 | 152 | 107 | 98 | 101 | 124 | 99 | 106 | 101 |
| MEAN WTS | PHV78 | 123 | 99 | 143 | 101 | 108 | 104 | 129 | 100 | 76 | 100 |
| | DIFF. | 4 | 10 | 8 | 6 | 10 | 3 | 5 | 0 | 30 | 1 |

| | INBRED | STA GRN | TST WTA | GRN QUL | SDG VGR | EST CNT | STK CNT | PLT HT | EAR HT | DRP EAR | BRT STK |
|---|---|---|---|---|---|---|---|---|---|---|---|
| TOTAL | REPLIC. | 4 | 19 | 19 | 4 | 11 | 19 | 4 | 4 | 14 | 2 |
| MEAN WTS | PHN46 | 88 | 98 | 94 | 99 | 103 | 100 | 102 | 110 | 101 | 101 |
| MEAN WTS | PHV78 | 83 | 97 | 88 | 104 | 103 | 100 | 104 | 105 | 99 | 101 |
| | DIFF. | 6 | 1 | 6 | 5 | 0 | 0 | 2 | 5 | 2 | |

TABLE 5

PHN46 HYBRID COMPARED TO PIONEER HYBRID 3374
VARIETY #1 - PHN46 HYBRID
VARIETY #2 - 3374

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 118 | 114 | 152.2 | 109 | 17.1 | 132.0 | 90.4 | 97.2 | 100.0 |
| | | 2 | 115 | 110 | 146.7 | 105 | 16.7 | 129.3 | 93.3 | 91.3 | 94.8 |
| | | LOCS | 1 | 1 | 6 | 6 | 6 | 2 | 5 | 3 | 1 |
| | | DIFF | 2 | 4 | 5.5 | 4 | 0.4 | 2.8 | 2.9 | 5.9 | 5.2 |
| | | PROB | | | .493 | .466 | .080* | .361 | .228 | .425 | |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 5.5 | 58.3 | 4.5 | 5.8 | 4.6 | 59.5 | 109.3 | 49.8 | 100.0 |
| | | 2 | 6.0 | 59.1 | 5.5 | 6.2 | 4.4 | 55.7 | 113.5 | 51.5 | 97.9 |
| | | LOCS | 2 | 6 | 1 | 6 | 4 | 7 | 2 | 2 | 5 |
| | | DIFF | 0.5 | 0.8 | 1.0 | 0.4 | 0.3 | 3.8 | 4.3 | 1.8 | 2.1 |
| | | PROB | .000# | .152 | | .695 | .731 | .001# | .416 | .395 | .075* |

*= 10% SIG
+= 5% SIG
= 1% SIG

TABLE 6

PHN46 HYBRID COMPARED TO PIONEER HYBRID 3504
VARIETY #1 - PHN46 HYBRID
VARIETY #2 - 3504

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 114 | 112 | 151.3 | 102 | 20.2 | 130.7 | 94.9 | 86.7 | 99.0 |
| | | 2 | 113 | 107 | 152.3 | 101 | 19.7 | 127.7 | 95.8 | 78.5 | 100.0 |
| | | LOCS | 2 | 2 | 14 | 14 | 14 | 4 | 10 | 8 | 1 |
| | | DIFF | 1 | 5 | 1.0 | 1 | 0.5 | 3.0 | 0.9 | 8.2 | 1.0 |
| | | PROB | .580 | .795 | .858 | .882 | .040+ | .173 | .550 | .154 | |

| YEAR | REGION | VAR # | STA GRN ABS | TST WTA ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 5.8 | 56.6 | 6.8 | 4.8 | 53.6 | 111.3 | 55.9 | 99.6 | 99.2 |
| | | 2 | 5.4 | 57.0 | 7.2 | 5.3 | 60.3 | 118.6 | 54.7 | 98.7 | 99.7 |
| | | LOCS | 8 | 14 | 14 | 8 | 9 | 5 | 5 | 8 | 4 |
| | | DIFF | 0.4 | 0.4 | 0.4 | 0.5 | 6.7 | 7.3 | 1.2 | 0.9 | 0.5 |
| | | PROB | .483 | .335 | .151 | .563 | .090* | .077* | .411 | .114 | .202 |

*= 10% SIG
+= 5% SIG
= 1% SIG

TABLE 7

PHN47 HYBRID COMPARED TO PIONEER HYBRID 3527
VARIETY #1 - PHN46 HYBRID
VARIETY #2 - 3527

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 117 | 113 | 163.1 | 109 | 18.6 | 137.8 | 89.6 | 94.4 | 100.0 |
| | | 2 | 112 | 108 | 152.6 | 102 | 17.5 | 133.5 | 88.8 | 77.1 | 94.8 |

TABLE 7-continued

PHN47 HYBRID COMPARED TO PIONEER HYBRID 3527
VARIETY #1 - PHN46 HYBRID
VARIETY #2 - 3527

|  |  |  |  |  |  |  |  |  |  |  |  |
|---|---|---|---|---|---|---|---|---|---|---|---|
|  |  | LOCS | 2 | 2 | 11 | 11 | 11 | 4 | 10 | 6 | 1 |
|  |  | DIFF | 5 | 6 | 10.5 | 7 | 1.1 | 4.3 | 0.8 | 17.2 | 5.2 |
|  |  | PROB | .003# | .691 | .116 | .091* | .000# | .065* | .870 | .090* |  |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|---|
| TOTAL SUM |  | 1 | 6.5 | 58.2 | 4.0 | 6.8 | 5.1 | 58.3 | 102.5 | 50.4 | 98.5 | 97.0 |
|  |  | 2 | 4.8 | 59.1 | 6.0 | 7.3 | 5.9 | 58.0 | 105.9 | 50.9 | 98.2 | 99.1 |
|  |  | LOCS | 3 | 11 | 1 | 11 | 5 | 9 | 4 | 4 | 9 | 1 |
|  |  | DIFF | 1.7 | 0.9 | 2.0 | 0.5 | 0.8 | 0.2 | 3.4 | 0.5 | 0.2 | 2.0 |
|  |  | PROB | .063* | .017+ |  | .365 | .374 | .729 | .078* | .707 | .698 |  |

*= 10% SIG
+= 5% SIG
= 1% SIG

TABLE 8

PHN46 HYBRID COMPARED TO PIONEER HYBRID 3362
VARIETY #1 - PHN46 HYBRID
VARIETY #2 - 3362

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM |  | 1 | 112 | 113 | 161.7 | 109 | 17.6 | 136.6 | 88.3 | 94.8 | 100.0 |
|  |  | 2 | 118 | 105 | 154.4 | 104 | 18.8 | 133.5 | 79.6 | 92.2 | 97.9 |
|  |  | LOCS | 2 | 2 | 11 | 11 | 11 | 4 | 10 | 6 | 1 |
|  |  | DIFF | 5 | 8 | 7.3 | 5 | 1.2 | 3.1 | 8.7 | 2.5 | 2.1 |
|  |  | PROB | .096* | .128 | .148 | .147 | .008# | .209 | .068* | .060* |  |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|---|
| TOTAL SUM |  | 1 | 4.7 | 56.9 | 6.0 | 5.7 | 5.0 | 59.6 | 106.8 | 53.3 | 99.2 | 96.9 |
|  |  | 2 | 3.3 | 57.8 | 2.5 | 6.5 | 5.6 | 57.6 | 101.6 | 47.0 | 98.6 | 99.1 |
|  |  | LOCS | 3 | 11 | 1 | 11 | 5 | 9 | 4 | 4 | 9 | 1 |
|  |  | DIFF | 1.3 | 0.9 | 3.5 | 0.8 | 0.6 | 2.0 | 5.1 | 6.3 | 0.6 | 2.2 |
|  |  | PROB | .270 | .000# |  | .158 | .414 | .022+ | .066* | .002# | .133 |  |

*= 10% SIG
+= 5% SIG
= 1% SIG

TABLE 9

PHN46 HYBRID COMPARED TO PIONEER HYBRID 3180
VARIETY #1 - PHN46 HYBRID
VARIETY #2 - 3180

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM |  | 1 | 118 | 114 | 152.2 | 109 | 17.1 | 132.0 | 89.3 | 97.2 | 100.0 |
|  |  | 2 | 128 | 93 | 139.5 | 100 | 19.2 | 136.8 | 84.1 | 71.5 | 99.0 |
|  |  | LOCS | 1 | 1 | 6 | 6 | 6 | 2 | 5 | 3 | 1 |
|  |  | DIFF | 10 | 21 | 12.6 | 9 | 2.1 | 4.8 | 5.2 | 25.7 | 1.0 |
|  |  | PROB |  |  | .097* | .134 | .006# | .282 | .109 | .355 |  |

| | | VAR | STA GRN | TST WTA | COB SC | GRN QUL | SDG VGR | EST CNT | PLT HT | EAR HT | DRP EAR |

TABLE 9-continued

PHN46 HYBRID COMPARED TO PIONEER HYBRID 3180
VARIETY #1 - PHN46 HYBRID
VARIETY #2 - 3180

| YEAR | REGION | # | ABS | ABS | ABS | ABS | ABS | ABS | ABS | ABS | ABS |
|---|---|---|---|---|---|---|---|---|---|---|---|
| TOTAL SUM | | 1 | 5.5 | 58.3 | 4.5 | 5.8 | 4.6 | 59.5 | 109.3 | 49.8 | 100.0 |
| | | 2 | 4.8 | 57.9 | 3.5 | 6.3 | 5.0 | 56.4 | 116.0 | 53.5 | 99.0 |
| | | LOCS | 2 | 6 | 1 | 6 | 4 | 7 | 2 | 2 | 5 |
| | | DIFF | 0.8 | 0.4 | 1.0 | 0.6 | 0.4 | 3.1 | 6.8 | 3.8 | 1.0 |
| | | PROB | .500 | .342 | | .509 | .689 | .079* | .246 | .344 | .089* |

*= 10% SIG
+= 5% SIG
= 1% SIG

TABLE 10

PHN46 HYBRID COMPARED TO PIONEER HYBRID 3344
VARIETY #1 - PHN46
VARIETY #2 - 3344

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 113 | 115 | 153.3 | 110 | 16.2 | 130.8 | 87.9 | 90.9 | 100.0 |
| | | 2 | 119 | 95 | 138.5 | 99 | 17.4 | 134.5 | 81.6 | 75.1 | 100.0 |
| | | LOCS | 1 | 1 | 6 | 6 | 6 | 2 | 5 | 3 | 1 |
| | | DIFF | 6 | 21 | 14.8 | 12 | 1.2 | 3.8 | 6.2 | 15.9 | 0.0 |
| | | PROB | | | .063* | .066* | .093* | .126 | .318 | .369 | |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 4.3 | 58.3 | 6.0 | 5.3 | 4.5 | 60.5 | 113.8 | 52.5 | 98.5 |
| | | 2 | 4.0 | 56.8 | 2.0 | 4.8 | 5.3 | 57.0 | 118.3 | 52.8 | 96.0 |
| | | LOCS | 2 | 6 | 1 | 6 | 4 | 7 | 2 | 2 | 5 |
| | | DIFF | 0.3 | 1.5 | 4.0 | 0.4 | 0.8 | 3.6 | 4.5 | 0.3 | 2.5 |
| | | PROB | .500 | .006# | | .497 | .375 | .003# | .205 | .942 | .070* |

*= 10% SIG
+= 5% SIG
= 1% SIG

DEPOSITS

Applicant has made a deposit of at least 2500 seeds of Inbred Corn Line PHN46 with the American Type Culture Collection (ATCC), Rockville, Md. 20852 U.S.A. ATCC Deposit No. 97133. The seeds deposited with the ATCC on May 1, 1995 were taken from the deposit maintained by Pioneer Hi-Bred International, Inc., 700 Capital Square. 400 Locust Street, Des Moines, Iowa 50309-2340 since prior to the filing date of this application. This deposit of the Inbred Corn Line PHN48 will be maintained in the ATCC depository, which is a public depositor, for a period of 30 years or 5 years after the most recent request, or for the effective life of the patent, whichever is longer, and will be replaced if it becomes non-viable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.). PHN46 is a U.S. Protected Variety under Plant Variety Protection Certificate No. 9000249.

What is claimed is:

1. Inbred corn seed designated PHN46, having the ATCC Accession No. 97133.

2. A corn plant and its parts produced by the seed of claim 1.

3. An inbred corn plant having all the physiological and morphological characteristics of the plant of claim 2.

4. A corn plant regenerated from the regenerable cells of a tissue culture of inbred corn plant PHN46 and having ATCC accession No. 91733, the regenerated plant being capable of expressing all the physiological and morphological characteristics of inbred corn plant PHN46 deposited under ATCC accession No. 91733.

5. A tissue culture of regenerable cells of corn plant PHN46 having ATCC accession No. 91733.

6. Tissue culture according to claim 4 comprising regenerable cells of a plant part selected from meristematic tissue, anthers, leaves, embryos, and pollen, and protoplasts thereof.

7. A process to produce a hybrid corn seed which gives rise to a hybrid corn plant having alleles which, when expressed, contribute to hybrids which are adapted to the central corn belt and which exhibit improvement in the traits of: yield, stay green, stalks and roots, compared to similarly adapted hybrids, comprising the steps of:

(a) planting, in pollinating proximity, seed of corn inbred line PHN46 having ATCC accession No. 91733 and another inbred line, not PHN46;

(b) cultivating corn plants resulting from said planting, said corn plants having a male and female reproductive system;

(c) inactivating the male reproductive system prior to pollination of the plants of either the female inbred line;

(d) allowing natural cross pollinating to occur between the inbred lines; and (e) harvesting seeds produced on said inactivated plants of the inbred line.

8. $F_1$ hybrid corn seed produced by crossing the inbred corn plant PHN46, having ATCC No. 91733, with another corn plant that is not PHN46, and plants and parts thereof produced from the $F_1$ hybrid seed.

* * * * *